United States Patent [19]

Ho

[11] 4,427,667

[45] Jan. 24, 1984

[54] 2,2-BIS(HALOALKENYL)-1-SUBSTITUTED-1-DIALKOXYPHOSPHOROETHYLENE FUNGICIDES

[75] Inventor: Andrew W. Ho, Pinole, Calif.

[73] Assignee: Chevron Research Company, San Francisco, Calif.

[21] Appl. No.: 361,651

[22] Filed: Mar. 25, 1982

[51] Int. Cl.$^3$ ............................................. A01N 57/18
[52] U.S. Cl. .................................. 424/210; 260/940; 260/941; 424/212
[58] Field of Search ................ 260/940, 941; 424/210, 424/212

[56] References Cited

U.S. PATENT DOCUMENTS 3,047,606 7/1962 Wadsworth, Jr. .................. 260/940
3,657,282 4/1972 Christensen et al. ............... 260/940

*Primary Examiner*—Anton H. Sutto
*Attorney, Agent, or Firm*—D. A. Newell; T. G. DeJonghe; L. S. Squires

[57] ABSTRACT

The 2,2-bis(haloalkenyl)-1-substituted-1-dialkoxyphosphoroethylene compounds of this invention are effective fungicides. In particular, some of the compounds of this invention are especially effective against Grape Downy Mildew.

15 Claims, No Drawings

2,2-BIS(HALOALKENYL)-1-SUBSTITUTED-1-DIALKOXYPHOSPHOROETHYLENE FUNGICIDES

BACKGROUND OF THE INVENTION

With the world more dependent for food on an ever decreasing amount of cultivated land, it is necessary to develop fungicides which protect crops from fungicidal destruction.

U.S. Pat. No. 3,761,596 discloses ethyl bis(allylthio)-methylidenemalonates and chloro analogs thereof as fungicidal.

U.S. Pat. No. 4,007,279 discloses 2,3-dicyano-5,6-dihydro-p-dithiin and its 5-alkyl derivatives as fungicidal.

SUMMARY OF THE INVENTION

The compounds of the present invention are represented by the formula:

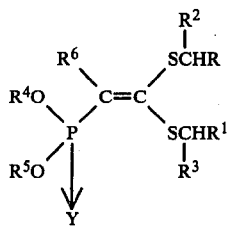

wherein
A.
  R and $R^1$ are independently
  1. lower alkenyl,
  2. lower alkynyl,
  3. lower alkenyl substituted with 1 to 3 of the same or different halogens, or
  4. lower alkynyl substituted with 1 to B 3 of the same or different halogens;
B.
  $R^2$ and $R^3$ are independently
  1. hydrogen or
  2. lower alkyl;
C. $R^4$ and $R^5$ are independently lower alkyl;
D. $R^6$ is
  1. cyano, or 2. 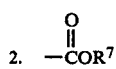
  $-\overset{\overset{O}{\|}}{C}OR^7$ wherein $R^7$ is lower alkyl; and
E.
  Y is either
  1. oxygen, or
  2. sulfur.

Among other factors, the present invention is based on my finding that the compounds of this invention are effective fungicides. Additionally, some of the compounds of this invention are especially effective against Grape Downy Mildew.

Due to their superior fungicidal activity, preferred R and $R^1$ groups are vinyl, vinyl substituted with 1 to 3 halogens, acetynyl, 2-butenyl, propargyl, and the like.

Particularly preferred R and $R^1$ groups include the vinyl groups substituted with 1 to 2 halo atoms.

Preferred halo groups are bromo and chloro.

Most preferably, R and $R^1$ are mono- and di-chlorinated vinyl groups.

Preferably, $R^2$ and $R^3$ are hydrogen.

Preferred $R^4$ and $R^5$ lower alkyl groups include, for instance, methyl, ethyl, n-propyl, isopropyl, and the like.

Most preferably $R^4$ and $R^5$ are both ethyl.

Preferred $R^6$ groups are cyano and

$-\overset{\overset{O}{\|}}{C}OR^7$.

Most preferably $R^6$ is cyano.

Preferred $R^7$ lower alkyl groups include, for instance, methyl, ethyl, n-propyl, isopropyl, and the like.

Most preferably $R^7$ is ethyl.

Most preferably Y is oxygen.

Definitions:

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 through 6 carbon atoms and includes primary, secondary, and tertiary alkyl groups. Typical lower alkyls include, for example, methyl, ethyl, n-propyl, isopropyl, n-butyl, t-butyl, n-hexyl, and the like.

The term "alkenyl" refers to unsaturated alkyl groups having a double bond (e.g., $CH_3CH=CH(CH_2)_2-$,) and includes both straight- and branched-chain alkenyl groups.

The term "lower alkenyl" groups refers to alkenyl groups having from 2 through 6 carbon atoms. Typical lower alkenyl groups include, for example, ethylene, but-3-enyl, hex-4-enyl, 2-methylpent-4-enyl, and the like.

The term "alkynyl" refers to unsaturated alkyl groups having a triple bond (e.g., $CH_3C\equiv C(CH_2)_2-$) and includes both straight- and branched-chain alkynyl groups.

The term "lower alkynyl" refers to alkynyl groups having from 2 through 6 carbon atoms and includes, for example, but-3-ynyl, hex-4-ynyl, 3-methylpent-4-ynyl, and the like.

The term "halo" or "halogen atom" refers to the groups fluoro, chloro, bromo and iodo.

The term "thioallyl" refers to the group:

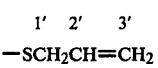
$\underset{1'\ \ 2'\ \ 3'}{-SCH_2CH=CH_2}$ with the conventional numbering system employed. Thus, the term "thio-3'-chloroallyl" refers to the group:

$-SCH_2CH=CHCl$.

The term "alkoxy" refers to the group $R^{10}O-$ wherein $R^{10}$ is alkyl.

The term "lower alkoxy" refers to alkoxy groups having 1 through 6 carbon atoms and includes, for example, methoxy, ethoxy, t-butoxy, hexoxy, and the like.

The term "phosphoro" refers to the P→O group while the term "thiophosphoro" refers to the P→S group.

The term "dialkoxyphosphoro" refers to the

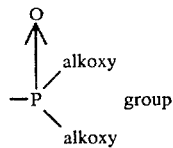

and includes, for example,

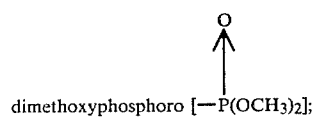

dimethoxyphosphoro [—P(OCH$_3$)$_2$];

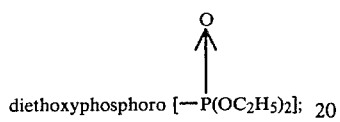

diethoxyphosphoro [—P(OC$_2$H$_5$)$_2$];

and the like.

The term "dialkoxythiophosphoro" refers to the

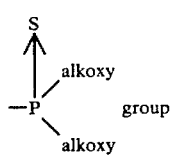

and includes, for example, dimethoxythiophosphoro, diethoxythiophosphoro, and the like.

The term "1-cyano-1-diethoxyphosphoro-2-thioallyl-2-(thio-3'-chloroallyl)ethylene" refers to the group:

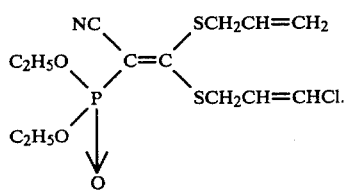

DETAILED DESCRIPTION OF THE INVENTION

The compounds of the present invention are prepared according to the following synthetic scheme:

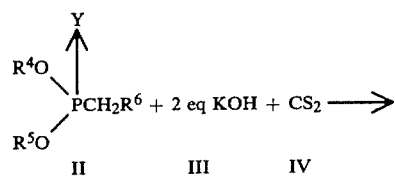

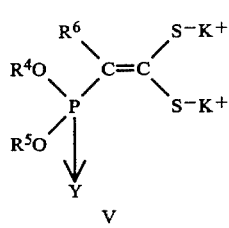

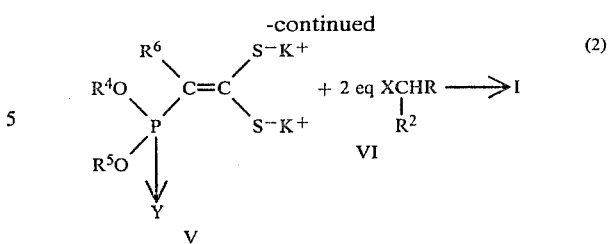

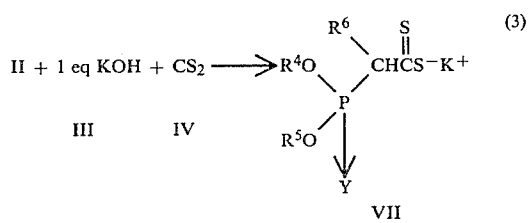

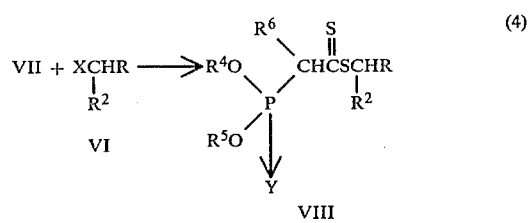

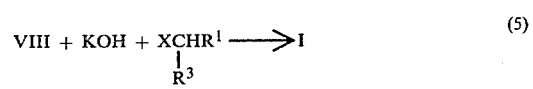

wherein R, R$^1$, R$^2$, R$^3$, R$^4$, R$^5$, R$^6$ and Y are as defined above and X is a halogen.

The compounds of Formula I wherein R and R$^1$ are identical to each other and R$^2$ and R$^3$ are identical to each other are conveniently prepared as shown in Reactions (1) and (2) above.

Reaction (1) is conveniently conducted by adding 2 to 2.5 equivalents of an inorganic base to the appropriate reagent, II. The reaction is done in the liquid phase employing an inert organic solvent such as dioxane, tetrahydrofuran, diethyl ether, dichloromethane, and the like. Suitable inorganic bases include, for instance, potassium hydroxide, sodium carbonate, potassium carbonate, and the like. Preferably, the reaction employs pulverized potassium hydroxide as the base in a dioxane medium. 1 to 2.5 equivalents of carbon disulfide, IV, is then added to the system. The reaction is generally conducted at from 0° to 100° C., although preferably at from 5° to 40° C. and is generally complete from within 1 to 24 hours. Reaction pressure is not critical and for convenience, the reaction is generally conducted at atmospheric pressure. The product, V, is then isolated by conventional procedures such as extraction, filtration, chromatography, distillation, or alternatively is used in Reaction (2) without purification and/or isolation.

Reaction (2) is conducted by adding 2.0 to 2.5 equivalents of the appropriate reagent, VI, to V. The reaction is conducted in the liquid phase employing an inert organic solvent such as dimethylformamide, toluene, methanol, and the like. Reaction pressure is not critical and for convenience, the reaction is generally conducted at atmospheric pressure. The reaction is generally conducted at from −10° to 50° C., although preferably at from 20° to 40° C. and is generally complete from within 1 to 48 hours. The product, I, is isolated by conventional procedures such as extraction, filtration, chromatography, distillation, and the like.

The synthesis of compounds of this invention wherein R and $R^1$ are not identical is depicted in Reactions (3), (4) and (5).

Reaction (3) is conveniently conducted by adding an essentially equimolar amount of an inorganic base to the appropriate reagent, II. The reaction is done in the liquid phase employing an inert organic solvent such as dioxane, tetrahydrofuran, dimethylformamide, and the like. Suitable inorganic bases include, for instance, potassium hydroxide, sodium carbonate, potassium carbonate, and the like. Preferably, the reaction employs pulverized potassium hydroxide as the base in a dimethylformamide medium. 1 to 2.5 equivalents of carbon disulfide, IV, is then added to the system. The reaction is generally conducted at from $-20°$ to $50°$ C., although preferably at from $-5°$ to $20°$ C. and is generally complete from within 1 to 24 hours. Reaction pressure is not critical and for convenience, the reaction is generally conducted at atmospheric pressure. The product, VII, is isolated by conventional procedures such as extraction, filtration, chromatography, distillation, and the like. Alternatively and preferably, the product, VII, is used directly in Reaction (4) using the same vessel and solvent.

Reaction (4) is conducted by adding an essentially equimolar amount of the appropriate reagent, VI, to VII. The reaction is conducted in the liquid phase employing an inert organic solvent such as dimethylformamide, dioxane, and the like. Preferably, the reaction solution is the same as was employed in Reaction (3) with the appropriate reagent VI merely added to the system after completion of Reaction (3). Reaction pressure is not critical and for convenience, the reaction is generally conducted at atmospheric pressure. The reaction is generally conducted at from $0°$ to $100°$ C., although preferably at from $15°$ to $25°$ C. and is generally complete from within 1 to 24 hours. The product, VIII, is isolated by conventional procedures such as extraction, filtration, chromatography, distillation, and the like. Alternatively and preferably, the product, VIII, is used directly in Reaction (5) using the same vessel and solvent.

Reaction (5) is conducted by adding an essentially equimolar amount of an inorganic base to VIII. The reaction is conducted in the liquid phase employing an inert organic solvent such as dimethylformamide, dioxane, and the like. Preferably, the base is added at from $0°$ to $5°$ C. to the same solution as was employed in Reaction (4) with the appropriate base merely added to the cooled system after completion of Reaction (4). Suitable inorganic bases include, for instance, potassium hydroxide, sodium carbonate, potassium carbonate, and the like. Preferably, the reaction employs pulverized potassium hydroxide as the base. After addition of the base, an essentially equimolar amount of the appropriate reagent, IX, is added. This reaction is generally conducted at from $0°$ to $100°$ C. and is generally complete from within 1 to 48 hours. Reaction pressure is not critical and for convenience, the reaction is generally conducted at atmospheric pressure. The product, I, is then isolated by conventional procedures such as extraction, filtration, chromatography, distillation, and the like.

Reactions (1), (3) and (5) involve the addition of a solid base to an organic solvent. In order to facilitate reaction completion, a phase-transfer catalyst is preferably employed in these reactions to aid in the transfer of the solid base into the organic solvent. Preferred catalysts include, for instance, tetraalkylammonium halides. A particularly preferred catalyst is tetra-n-butylammonium bromide. In general, 0.025 equivalents of the catalyst have been found sufficient to accomplish the catalytic effect desired.

Alternatively, if the base employed is in an aqueous solution, a phase-transfer catalyst is employed to facilitate transfer from the aqueous phase to the organic phase.

Reactions (2) and (4) involve adding a potassium thiolate to an organic medium. Preferably, in order to speed the time required for reaction, a catalytic amount ($\sim$0.025 equivalents) of a phase-transfer catalyst is added. Catalysts such as tetraalkylammonium halide salts are preferred.

Utility:

The compounds of this invention are useful for controlling fungi. Additionally, some of the compounds are useful in controlling leaf blights caused by such organisms as *Phytophthora infestans conidia, Alternaria solani conidia, Septoria apii*, downy mildew caused by organisms such as *Plasmopara viticola*, and other fungal infections caused by organisms such as *Piricularia oryzae* and *Erysiphe polygoni*.

However, some fungicidal compounds of the invention may be more fungicidally active than others against particular fungi. Table II lists a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperatures and temperature ranges refer to the centigrade system and the term "ambient" or "room temperature" refers to about 20° to 25° C. The term "percent" refers to weight percent and the term "mol" or "mols" refers to gram mols. The term "equivalent" refers to a reagent equal in mols, to the mols of the preceding or succeeding reactant recited in that example in terms of finite mols or finite weight or volume. Unless expressly stated to the contrary, geometric isomer and racemic mixtures are used as starting materials and correspondingly isomer mixtures are obtained as products. Also, unless expressly stated to the contrary, mixtures of E and Z isomers are generated whenever possible and are not separated.

Compounds which were prepared in accordance with Examples 1 to 5 below are found in Table I.

EXAMPLE 1

Preparation of 1-cyano-1-diethoxyphosphoro-2,2-bis(thio-3'-cis-chloroallyl)ethylene To a suspension of 13.6 gm of pulverized potassium hydroxide in 150 ml of dioxane was added 17.7 gm of diethoxyphosphorocyanomethane over 1 hour. Afterwards, 10 ml of carbon disulfide was added. The system was stirred at room temperature for 18 hours and then the system was diluted with 150 ml of ether. The resulting precipitate was filtered and washed with ether. The product was then suspended in 150 ml of dimethylformamide. 27.7 gm of cis-1,3-dichloropropene was slowly added to the system at from 0° to 10° C. The system was stirred at 50° C. for 24 hours and the solution then poured into water. The product was extracted with ethyl ether. The product was separated and purified by column chromatography using silica gel and 20% ethyl acetate-hexane as the eluant. The product was isolated and the solvent removed to give the 1-cyano-1-diethoxyphosphoro-2,2-bis(thio-3'-chloroallyl)ethylene as a brown oil. Listed as Compound No. 1 in Table I.

EXAMPLE 2

Preparation of 1-cyano-1-diethoxyphosphoro-2-thioallyl-2-(thio-3'-chloroallyl)ethylene (a) 17.7 gm of

diethoxyphosphorocyanomethane [(CH$_3$O)$_2$PCH$_2$CN]

in 30 ml of dimethylformamide is added dropwise at 0° C. to a suspension of 6.7 gm of pulverized potassium hydroxide in 150 ml of dimethylformamide. The mixture is stirred at this temperature for 30 minutes. Afterwards, 7.5 ml of carbon disulfide is slowly added to the system. The system is warmed to room temperature and stirred there for 3 hours. 12.2 gm of allyl bromide is then added to the system. The system is stirred at room temperature for 16 hours to give the 1-cyano-1-diethoxyphosphoro-dithioacetic acid allyl ester.

(b) To the system containing the 1-cyano-1-diethoxyphosphoro-dithioacetic acid allyl ester is added 6.7 gm of pulverized potassium hydroxide at 0° C. The system is stirred for ½ hour and then 11.6 gm of 1,3-dichloropropene is added. The system is stirred for 6 hours and then poured into water. The product is extracted with ether and the ethereal extract first washed with sodium bicarbonate solution and then with brine. The ethereal solution is then dried over magnesium sulfate and the ether removed by stripping to give the crude product. The product is separated and purified by chromatography to give the title compound.

EXAMPLE 3

Preparation of 1-ethoxycarbonyl-1-diethoxyphosphoro-2,2-bis(thio-2'-chloroallyl)ethylene To a suspension of 6.8 gm of pulverized potassium hydroxide in 100 ml of dioxane was added 11.2 gm of

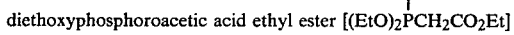

diethoxyphosphoroacetic acid ethyl ester [(EtO)$_2$PCH$_2$CO$_2$Et]

over 2 hours. Afterwards, 6 ml of carbon disulfide was added. The system was stirred at room temperature for 18 hours and then the system was diluted with 100 ml of ether. The resulting precipitate was filtered and washed with ether. The product was then suspended in 70 ml of dimethylformamide. 1,3-Dichloropropene was slowly added to the system at from 0° to 10° C. The system was stirred at 80° C. for 24 hours and the solution then poured into water. The product was extracted with ethyl acetate. The product was separated and purified by column chromatography using silica gel and ethyl acetate as the elutant. The product was isolated and the solvent removed to give the 1-ethoxycarbonyl-1-diethoxyphosphoro-2,2-bis(thio-3'-chloroallyl)ethylene as a yellow oil. Listed as Compound No. 9 in Table I.

EXAMPLE 4

Preparation of 1-methoxycarbonyl-1-diethoxyphosphoro-2,2-bis[thio-(1'-methyl-2'-chloroallyl)]ethylene To a suspension of 11.2 gm of pulverized potassium hydroxide in 200 ml of dioxane is added 21.0 gm of diethoxyphosphoroacetic acid methyl ester over 2 hours. Afterwards, 10 ml of carbon disulfide is added. The system is stirred at room temperature for 16 hours and then the system is diluted with 300 ml of ether. The resulting precipitate is filtered and washed with water. The product is then suspended in 150 ml of dimethylformamide. 25.0 gm of 2,3-dichlorobut-1-ene is slowly added to the system at 0° C. to 10° C. The system is stirred for 16 hours and the solution is then poured into water. The product is separated and purified by column chromatography. The product is isolated and the solvent removed to give the 1-methoxycarbonyl-1-diethoxyphosphoro-2,2-bis[thio-(1'-methyl-2'-chloroallyl)]ethylene, i.e., 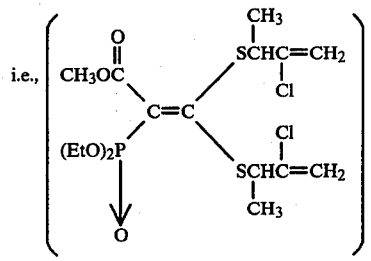

EXAMPLE 5

Preparation of 1-ethoxycarbonyl-1-diethoxythiophosphoro-2,2-bis(thio-2'-bromoallyl)ethylene To a suspension of 12 gm of pulverized potassium hydroxide in 100 ml of dioxane is added 24 gm of diethoxythiophosphoroacetic acid ethyl ester over 1 hour. Afterwards, 5 ml of carbon disulfide is added. The system is stirred at room temperature for 16 hours and then the system is diluted with 150 ml of ether. The resulting precipitate is filtered and washed with ether. The product is then suspended in 150 ml of dimethylformamide.

20.5 gm of 2,3-dibromopropene is slowly added to the system at from 0° to 10° C. The system is stirred at 80° C. for 24 hours and the solution then poured into water. The product is extracted with ether. The product is separated and purified by column chromatography. The product is isolated and the solvent removed to give the title compound.

Compounds which are prepared in accordance with Examples 1 to 5 above include, for instance:

1-cyano-1-diethoxyphosphoro-2,2-bis(thio-3'-chloroallyl)ethylene;
1-cyano-1-diethoxythiophosphoro-2,2-bis(thio-3'-chloroallyl)ethylene;
1-cyano-1-dimethoxyphosphoro-2-thioallyl-2-(thio-3'-chloroallyl)ethylene;
1-cyano-1-di-n-propoxyphosphoro-2-thioallyl-2-(thio-3'-bromoallyl)ethylene;
1-cyano-1-dimethoxythiophosphoro-2-thioallyl-2-(thio-3'-bromoallyl)ethylene;
1-cyano-1-dihexoxythiophosphoro-2,2-bis(thio-2'-bromoallyl)ethylene;
1-cyano-1-diethoxythiophosphoro-2,2-bis(thio-2',3'-dichloroallyl)ethylene;
1-methoxycarbonyl-1-diethoxyphosphoro-2,2-bis(thio-3'-chloroallyl)ethylene;
1-ethoxycarbonyl-1-diethoxythiophosphoro-2,2-bis(thio-3'-chloroallyl)ethylene;
1-n-propoxycarbonyl-1-dimethoxyphosphoro-2-thioallyl-2-(thio-3'-chloroallyl)ethylene;
1-ethoxycarbonyl-1-di-n-propoxyphosphoro-2-thioallyl-2-(thio-3'-bromoallyl)ethylene;
1-ethoxycarbonyl-1-dimethoxythiophosphoro-2-thioallyl-2-(thio-3'-bromoallyl)ethylene; and
1-ethoxycarbonyl-1-diethoxythiophosphoro-2,2-bis(thio-2'-bromoallyl)ethylene;
1-ethoxycarbonyl-1-diethoxyphosphoro-2,2-bis(thiopropargyl)ethylene.

EXAMPLE 6

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° to 80° F.; relative humidity was maintained at 40% to 60%. The percent disease control provided by a given test compound was based on the percent disease reduction relative to the untreated check plants. The results are tabulated in Table II.

EXAMPLE 7

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE 8

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE 9

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in an environmental chamber and incubated at 66° to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMPLE 10

Grape Downy Mildew

The compounds of the invention were tested for the control of the Grape Downy Mildew organism *Plasmopara viticola*. Detached leaves, between 70 and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66° to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE 11

Leaf Rust

The Leaf Rust test was made using pinto beans. The pathogen was *Uronyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

EXAMPLE 12

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants.

$$\% \text{ Control} = 100 \times \left( \frac{\% \text{ disease in treated plants}}{\% \text{ disease in check}} \right)$$

The results are tabulated in Table II.

TABLE I
COMPOUNDS OF THE FORMULA

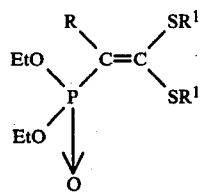

| Compound No. | R | R$^1$ | Carbon Calc. | Carbon Found | Hydrogen Calc. | Hydrogen Found | Nitrogen Calc. | Nitrogen Found | Form |
|---|---|---|---|---|---|---|---|---|---|
| 1 | —CN | —CH$_2$–C(H)=C(Cl)(H) (cis) | 38.81 | 38.95 | 4.51 | 4.60 | 3.48 | 3.47 | oil |
| 2 | —CN | —CH$_2$CCl=CHCl | 33.14 | 31.16 | 3.42 | 3.47 | 2.97 | 2.88 | oil |
| 3 | —CN | —CH$_2$–C(Cl)=CH$_2$ | 38.81 | 38.93 | 4.51 | 4.41 | 3.48 | 3.43 | oil |
| 4 | —CN | —CH$_2$–C(H)=C(H)(Cl) (trans) | 38.81 | 37.51 | 4.51 | 4.55 | 3.48 | 3.56 | oil |
| 5 | —CN | —CH$_2$CH=CHCH$_3$ | 49.84 | 49.74 | 6.69 | 6.92 | 3.88 | 3.77 | oil |
| 6 | EtOC(O)— | —CH$_2$–C(H)=C(H)(Cl) (trans) | 40.09 | 36.46 | 5.16 | 4.72 | | | oil |
| 7 | EtOC(O)— | —CH$_2$–C(H)=C(Cl)(H) (cis) | 40.09 | 36.92 | 5.16 | 4.68 | | | oil |
| 8 | EtOC(O)— | —CH$_2$–C(Cl)=CHCl | 34.76 | 31.20 | 4.08 | 3.44 | | | oil |
| 9 | EtOC(O)— | —CH$_2$–C(Cl)=CH$_2$ | 40.09 | 36.06 | 5.16 | 4.53 | | | oil |
| 10 | EtOC(O)— | —CH$_2$CH=CHCH$_3$ | 49.98 | 46.90 | 7.10 | 5.80 | | | oil |

TABLE II
FUNGICIDAL ACTIVITY
ACTIVITY IN TERMS OF % CONTROL

| Compound No. | GDM | TLB | CLB | TEB | BR | BPM | RB |
|---|---|---|---|---|---|---|---|
| 1 | 63 | 57 | 46 | 0 | 0 | 16 | 13 |
| 2 | 98 | 64 | 50 | 21 | 0 | 0 | — |
| 3 | 69 | 19 | 67 | 29 | 0 | 0 | — |
| 4 | 78 | 50 | 33 | 0 | 0 | 0 | 28 |
| 5 | 8 | 0 | 62 | 0 | 0 | 0 | 20 |
| 6 | 11 | 32 | 0 | 23 | 0 | 0 | — |
| 7 | 0 | 18 | 0 | 27 | 0 | 0 | — |
| 8 | 11 | 0 | 13 | 14 | 0 | 0 | — |

TABLE II-continued

FUNGICIDAL ACTIVITY
ACTIVITY IN TERMS OF % CONTROL

| Compound No. | GDM | TLB | CLB | TEB | BR | BPM | RB |
|---|---|---|---|---|---|---|---|
| 9 | 25 | 21 | 0 | 5 | 0 | 0 | — |
| 10 | 6 | 25 | 0 | 11 | 0 | 0 | — |

GDM—Grape Downy Mildew (*Plasmopara viticola*)
TLB—Tomato Late Blight (*Phytophthora infestans conidia*)
CLB—Celery Late Blight (*Septoria apii*)
TEB—Tomato Early Blight (*Alternaria solani conidia*)
BR—Bean Rust Eradicant (*Uronyces phaseoli tipica*)
BPM—Bean Powdery Mildew (*Erysiphe polygoni*)
RB—Rice Blast (*Piricularia oryzae*)

What is claimed is:

1. A compound having the formula:

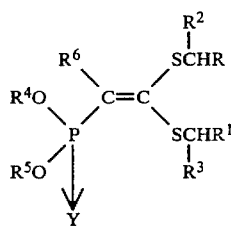 (I)

wherein
R and $R^1$ are independently lower alkenyl or lower alkenyl substituted with 1 to 3 of the same or different halogens;
$R^2$ and $R^3$ are independently hydrogen or lower alkyl;
$R^4$ and $R^5$ are independently lower alkyl;
$R^6$ is cyano or —$COOR^7$ wherein $R^7$ is lower alkyl; and
Y is oxygen or sulfur.

2. A method for controlling fungi which comprises applying to the fungus or its habitat a fungicidally effective amount of the compound of the formula defined in claim 1.

3. A compound of the formula described in claim 1 wherein $R^2$ and $R^3$ are hydrogen.

4. A compound of the formula described in claim 3 wherein R and $R^1$ are lower alkenyl.

5. A compound of the formula described in claim 4 wherein R and $R^1$ are vinyl.

6. A compound of the formula described in claim 3 wherein R and $R^1$ are lower alkenyl substituted with 1 to 3 of the same or different halogens.

7. A compound of the formula described in claim 6 wherein R and $R^1$ are vinyl substituted with 1 or 2 chloro groups.

8. A compound of the formula described in claim 3 wherein $R^4$ and $R^5$ are ethyl.

9. A compound of the formula described in claim 8 wherein Y is oxygen.

10. A compound of the formula described in claim 9 wherein $R^6$ is cyano.

11. A compound of the formula described in claim 9 wheein $R^6$ is

wherein $R^7$ is lower alkyl.

12. A compound of the formula described in claim 11 wherein $R^7$ is ethyl.

13. A compound of the formula described in claim 10 wherein R and $R^1$ are both —CCl=CHCl.

14. A compound of the formula described in claim 12 wherein R and $R^1$ are both —CH=CHCl.

15. A fungicidal composition comprising a biologically inert carrier and a fungicidally effective amount of the compound defined in claim 1.

* * * * *